US011068056B2

(12) United States Patent
Nie

(10) Patent No.: US 11,068,056 B2
(45) Date of Patent: *Jul. 20, 2021

(54) WEARABLE EYE TRACKING SYSTEM WITH SLIPPAGE DETECTION AND CORRECTION

(71) Applicant: Xiaochun Nie, Mountain View, CA (US)

(72) Inventor: Xiaochun Nie, Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/903,986

(22) Filed: Jun. 17, 2020

(65) Prior Publication Data

US 2020/0319708 A1      Oct. 8, 2020

Related U.S. Application Data

(63) Continuation of application No. 16/016,596, filed on Jun. 23, 2018.

(60) Provisional application No. 62/527,562, filed on Jun. 30, 2017.

(51) Int. Cl.

| G06F 3/01 | (2006.01) |
|---|---|
| G06T 7/73 | (2017.01) |
| G06T 7/13 | (2017.01) |
| G06T 7/246 | (2017.01) |
| G06K 9/00 | (2006.01) |
| A61B 3/113 | (2006.01) |

(52) U.S. Cl.
CPC .............. *G06F 3/013* (2013.01); *A61B 3/113* (2013.01); *G06F 3/012* (2013.01); *G06K 9/0061* (2013.01); *G06K 9/00281* (2013.01); *G06T 7/13* (2017.01); *G06T 7/248* (2017.01); *G06T 7/74* (2017.01); *G06T 2207/30041* (2013.01); *G06T 2207/30201* (2013.01)

(58) Field of Classification Search
CPC .. G06T 7/74; G06T 7/248; G06T 7/13; G06T 2207/3004; G06T 2207/30201; G06K 9/00281; G06K 9/0061; A61B 3/113; G06F 3/012; G06F 3/013
See application file for complete search history.

(56) References Cited

U.S. PATENT DOCUMENTS

| 2012/0133891 | A1* | 5/2012 | Jiang | A61B 3/0025 351/210 |
|---|---|---|---|---|
| 2013/0050070 | A1* | 2/2013 | Lewis | G06K 9/00604 345/156 |
| 2013/0083976 | A1* | 4/2013 | Ragland | A61B 3/113 382/117 |
| 2013/0178287 | A1 | 7/2013 | Yahav | |

* cited by examiner

*Primary Examiner* — Casey L Kretzer
(74) *Attorney, Agent, or Firm* — IPro, PLLC

(57) ABSTRACT

Apparatus, systems and methods configured for eye tracking with slippage detection and correction are disclosed. In one example, a method comprises: obtaining a first image and a second image of a person's eye, with an imaging sensor; determining a position relationship between an eyeball center of the eye and the imaging sensor based on the first image and the second image.

16 Claims, 13 Drawing Sheets

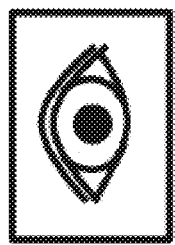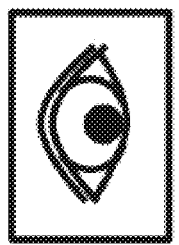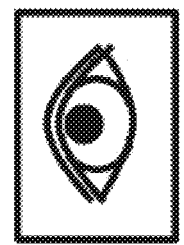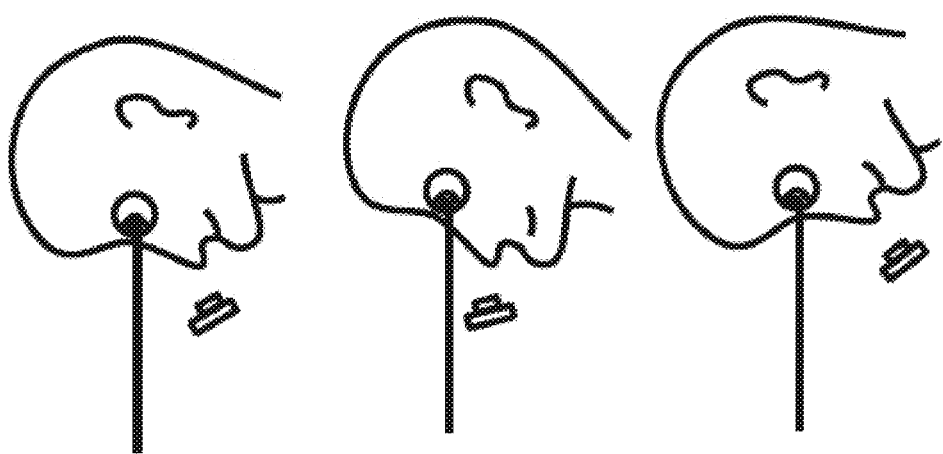
Fig. 9

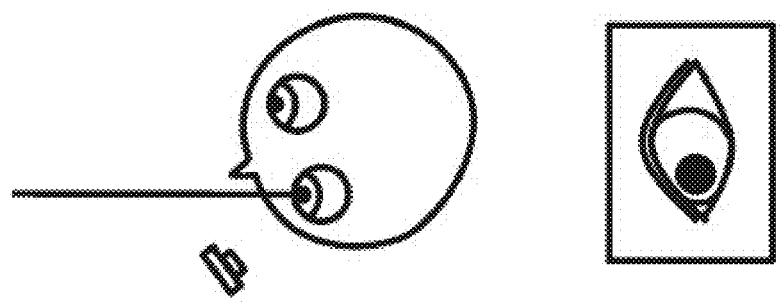
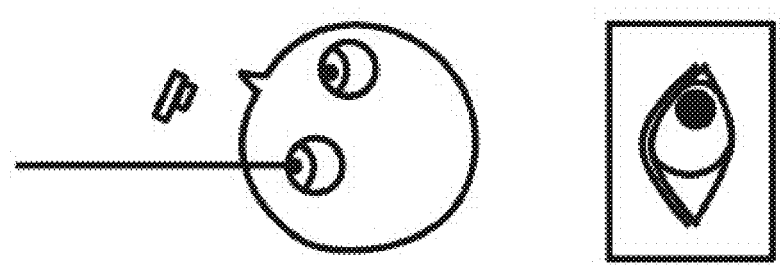
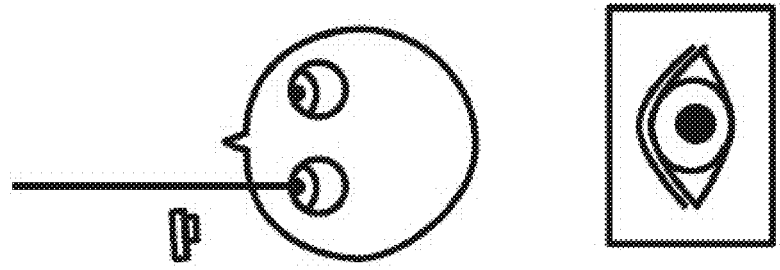
Images taken by the Camera
Fig. 10

WEARABLE EYE TRACKING SYSTEM WITH SLIPPAGE DETECTION AND CORRECTION

CROSS-REFERENCE TO RELATED APPLICATIONS

The disclosure of U.S. Provisional Application No. 62/527,562 is hereby incorporated by reference in its entirety.

TECHNICAL FIELD

This disclosure relates to a wearable eye motion tracking system with slippage detection and correction and methods for setting up and operations.

BACKGROUND

Human computer interaction (HCI), or generally human machine interaction, focuses on design and use of computer technology as well as interfaces between a user and a computer. HCI depends on responsive, intuitive and accurate measurements of human input actions. Mouse, Keyboard and touch screen are conventional input devices that require user's hands-on controls. Some input devices like Microsoft Kinect® are capable of tracking the user's body or hand gestures without any physical contact. The word "user" and the word "person" may be used interchangeably in this disclosure.

The recent progress in virtual reality (VR) brought VR goggles to consumer market. VR goggles can create immersive three-dimensional (3D) experience to the user. The user can look around in virtual world by a turn of the head just like looking around in the real world.

Augmented reality (AR) is another area that is progressing fast. One major difference between AR and VR is that AR operates in real-time on real world scenes as opposed to solely computer created or recorded scenes in VR. In both VR and AR, it will be very useful to know where the user is looking at and what actions the user wants to take on the intended targets. Effective and reliable eye tracking will enable a broad range of applications under such circumstances.

Self-driving vehicles are also taking the front stage nowadays. There are situations where a car in its autonomous mode might need a driver's attention due to updated road or traffic conditions or driving mode changes. As such, it is useful to constantly monitor where the driver is looking at.

Machine learning and artificial intelligence (AI) may work in a cycle of learning, modeling and predicting. Quick and intuitive tracking the user's attention point for data acquisition and confirmation can play an important role in this loop.

SUMMARY

Disclosed herein is a method comprising: obtaining a first image and a second image of a person's eye, with an imaging sensor; determining a position relationship between an eyeball center of the eye and the imaging sensor based on the first image and the second image.

According to an embodiment, the method further comprises determining a relative movement of the imaging sensor with respect to the eyeball center based on the position relationship.

According to an embodiment, the first image and the second image are different.

According to an embodiment, determining the position relationship comprises extracting contours of a pupil or a corneal limbus from the first image and the second image, and determining the position relationship based on the contours.

According to an embodiment, determining the position relationship based on the contours comprises determining a location of the eyeball center in a 2D image plane of the imaging sensor based on the contours.

According to an embodiment, the first image and the second image are obtained during an intentional or random movement of the eye.

According to an embodiment, the method further comprises determining an orientation relationship between the imaging sensor and the person's head.

According to an embodiment, determining the orientation relationship comprises: obtaining a first set of gaze vectors while the person's head rotates about a first axis and the eye maintains a first gaze point; obtaining a second set of gaze vectors while the person's head rotates about a second axis and the eye maintains a second gaze point, or obtaining a third gaze vector while the eye maintains a third gaze point; determining the orientation relationship based on the first set of gaze vectors, and based on the second set of gaze vectors or the third gaze vector.

According to an embodiment, the imaging sensor comprises more than one camera.

According to an embodiment, the imaging sensor is configured to obtain an image of more than one eye of the person.

Disclosed herein is an apparatus comprising: an imaging sensor configured to obtain a first image and a second image of a person's eye; and a computing device comprising a processor configured to determine a position relationship between an eyeball center of the eye and the imaging sensor based on the first image and the second image.

According to an embodiment, the processor is further configured to determine a relative movement of the imaging sensor with respect to the eyeball center based on the position relationship.

According to an embodiment, the first image and the second image are different.

According to an embodiment, the processor is further configured to determine the position relationship by extracting contours of a pupil or a corneal limbus from the first image and the second image, and by determining the position relationship based on the contours.

According to an embodiment, the processor is further configured to determine the position relationship based on the contours by determining a location of the eyeball center in a 2D image plane of the imaging sensor based on the contours.

According to an embodiment, the imaging sensor is configured to obtain the first image and the second image during an intentional or random movement of the eye.

According to an embodiment, the processor is further configured to determine an orientation relationship between the imaging sensor and the person's head.

According to an embodiment, the processor is further configured to determine the orientation relationship by: obtaining a first set of gaze vectors while the person's head rotates about a first axis and the eye maintains a first gaze point; obtaining a second set of gaze vectors while the person's head rotates about a second axis and the eye maintains a second gaze point, or obtaining a third gaze vector while the eye maintains a third gaze point; determining the orientation relationship based on the first set of gaze vectors, and based on the second set of gaze vectors or the third gaze vector.

According to an embodiment, the imaging sensor comprises more than one camera.

According to an embodiment, the imaging sensor is configured to obtain an image of more than one eye of the person.

Disclosed herein is a method comprising: obtaining a first set of images of a person's eye, using an imaging sensor, while the person's head rotates about a first axis and the eye maintains a first gaze point; obtaining a second set of images of the eye, using the imaging sensor, while the person's head rotates about a second axis and the eye maintains a second gaze point, or obtaining a third image, using the imaging sensor, while the eye maintains a third gaze point; determining an orientation relationship between the imaging sensor and the person's head, based on the first set of images, and based on the second set of images or the third image.

According to an embodiment, the method further comprises: obtaining a first set of gaze vectors based on the first set of images; obtaining a second set of gaze vectors based on the second set of images or obtaining a third gaze vector based on the third image; determining the orientation relationship is based on the first set of gaze vectors, and based on the second set of gaze vectors or the third gaze vector.

According to an embodiment, the first gaze point and the second gaze point are different, or the first gaze point and the third gaze point are different.

According to an embodiment, the imaging sensor comprises more than one camera.

According to an embodiment, the imaging sensor is configured to obtain an image of more than one eye of the person.

Disclosed herein is an apparatus comprising: an imaging sensor; and a computing device comprising a processor. The imaging sensor is configured to obtain a first set of images of a person's eye, while the person's head rotates about a first axis and the eye maintains a first gaze point. The imaging sensor is configured to obtain a second set of images of the eye, while the person's head rotates about a second axis and the eye maintains a second gaze point, or to obtain a third image, while the eye maintains a third gaze point. The computing device comprising the processor is configured to determine an orientation relationship between the imaging sensor and the person's head based on the first set of images, and based on the second set of images or the third image.

According to an embodiment, the processor is configured to: obtain a first set of gaze vectors based on the first set of images; obtain a second set of gaze vectors based on the second set of images, or obtain a third gaze vector based on the third image; and determine the orientation relationship based on the first set of gaze vectors, and based on the second set of gaze vectors or the third gaze vector.

According to an embodiment, the first gaze point and the second gaze point are different or the first gaze point and the third gaze point are different.

According to an embodiment, the imaging sensor comprises more than one camera.

According to an embodiment, the imaging sensor is configured to obtain an image of more than one eye of the person.

Disclosed herein is a method comprising: obtaining a first image of a person's eye, with an imaging sensor; extracting a contour of a pupil or a corneal limbus from the first image; determining a location of an eyeball center of the eye in a 2D image plane of the imaging sensor; determining a position relationship between the eyeball center and the imaging sensor based on the contour and the location.

According to an embodiment, determining the location comprises extracting contours of the pupil or corneal limbus from two images of the eye obtained with the imaging sensor.

According to an embodiment, the first image is one of the two images.

Disclosed herein is an apparatus comprising: an imaging sensor configured to obtain images of a person's eye; a computing device comprising a processor configured to extract a contour of a pupil or a corneal limbus from at least one of the images, to determine a location of an eyeball center of the eye in a 2D image plane of the imaging sensor, and to determine a position relationship between the eyeball center and the imaging sensor based on the contour and the location.

According to an embodiment, the processor is configured to determine the location by extracting contours of the pupil or corneal limbus from at least two of the images.

BRIEF DESCRIPTION OF FIGURES

FIG. 9 shows the first step of one calibration process.

FIG. 10 shows the second step of the calibration process.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components have been described at a relatively high-level, without detail, in order to avoid unnecessarily obscuring aspects of the present teachings.

A 3D coordinate system using the right hand rule is defined in Part A1.1 of the Appendix section. A 2D coordinate system for camera image frame is defined in Part A1.2 of the Appendix section.

Mathematical utility functions used in this disclosure are listed in Part A2, Part A3, and Part A4 of the Appendix section. Quaternion, vector and matrix mathematics is discussed herein. Quaternions are widely used in this disclosure. A function using quaternions can also be expressed using matrices, Euler angles or other suitable mathematic expressions.

Figure 6:
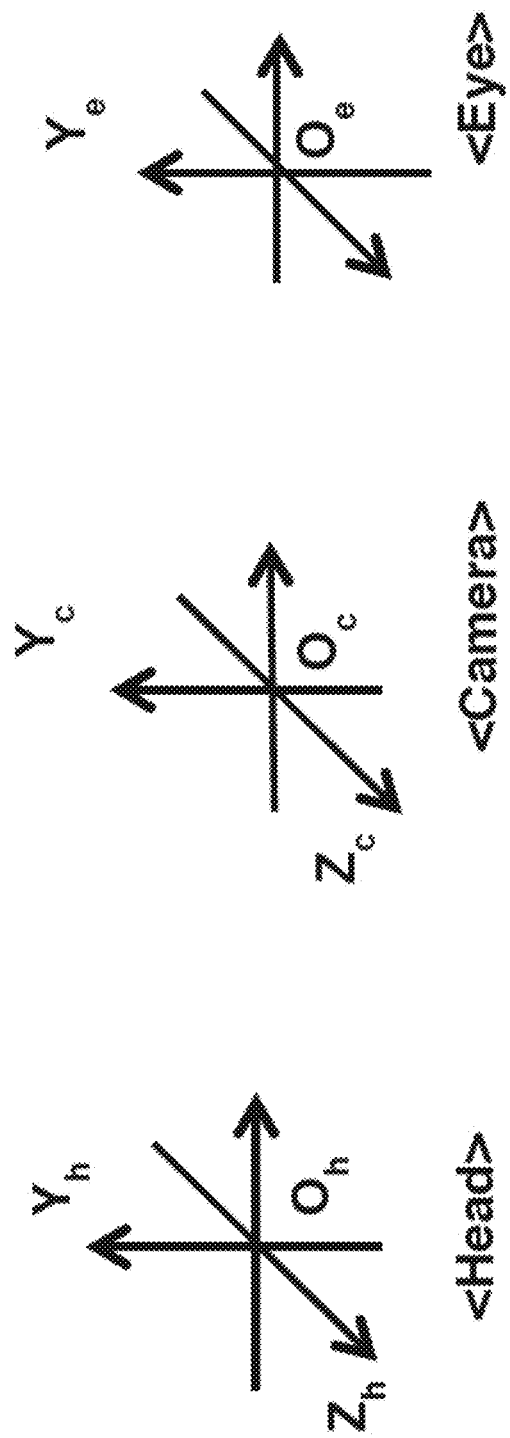
FIG. 6 shows that three 3D coordinate systems referred to herein: the head coordinate system; the camera coordinate system; and the eye coordinate system.

There are three 3D coordinate systems referred to in this disclosure as shown in FIG. 6: the head coordinate system Xh-Yh-Zh-Oh, abbreviated as CS-H; the camera coordinate system Xc-Yc-Zc-Oc, abbreviated as CS-C; the eye coordinate system Xe-Ye-Ze-Oe, abbreviated as CS-E. The origin of CS-E is at the center of an eyeball of a person. The unit of CS-C and CS-E is the radius of the eyeball. The containing order of these coordinate systems is: CS-H>CS-C>CS-E.

Figure 7:
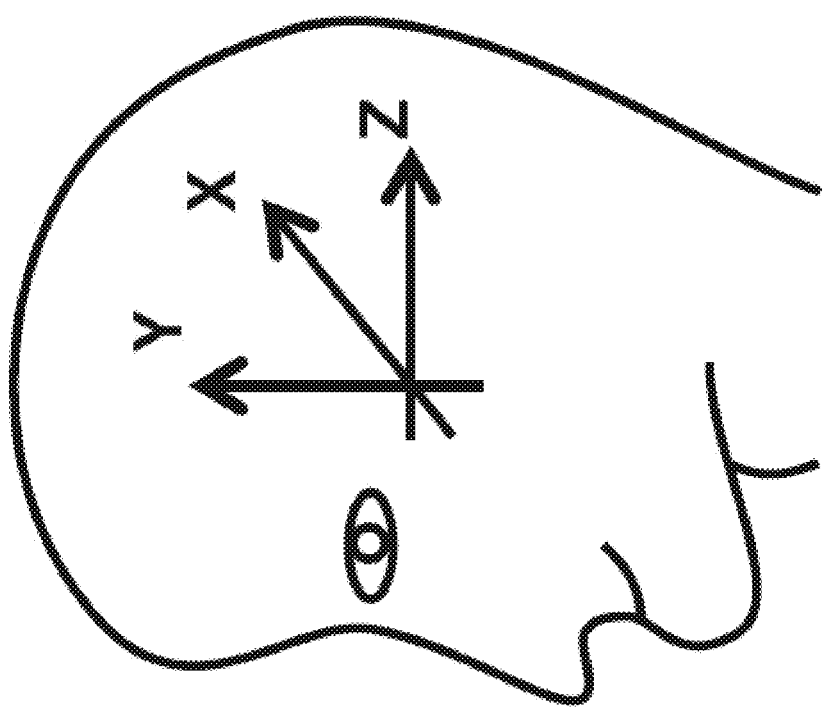
FIG. 7 shows the head coordinate system.

The head coordinate system CS-H is shown in FIG. 7. The X axis points from the user's left ear to the right ear; the Y axis points from bottom of the jaw to the top of the head; and the Z axis points from the tip of the nose to the back of the head. As a result, the X axis aligns with the normal sense of the left-to-right horizontal direction, the Y axis aligns with the normal sense of the vertical direction, and the Z axis aligns with the normal sense of the front-to-back horizontal direction. The directions of rotation about its axes are defined in Part A1.1 of the Appendix section.

The eye coordinate system CS-E is fixed to an eye of the user. When the eye is in its primary position (i.e., the eye looking straight ahead), the X, Y and Z axes of the CS-E respectively point to the same directions as the X, Y and Z axes of CS-H.

In abbreviations in the form of "ABC" used in this disclosure: A represents the type; B represents the specific; C represents the context. As an example, an abbreviation "qch" means a quaternion "q" representing the orientation of a camera "c" in the head coordinate system "h." See Part A2 of the Appendix section.

A gaze line is the line passing the center of the eyeball and the center of the pupil.

A gaze vector is a unit vector pointing from the origin of CS-E to the negative direction of the Z axis of CS-E. The gaze vector represents the direction of the gaze line.

A gaze point is a point on which the user's gaze line lands.

Stare is a condition when the gaze vector or the gaze point is limited in a small range over a period of time.

Using an image sensor (e.g., a video camera) facing the user's eye at a fixed position and orientation relative to the user's head, the following can be achieved. The word "image sensor" and the word "camera" may be used interchangeably in this disclosure. The word "image sensor" is not limited to a still camera.

From two or more images of the user's eye, using ellipses extracted from either the contour of the pupil or limbus, the position of the eyeball center in the camera coordinate system CS-C can be calculated. There is no specific requirement on the actions the user needs to perform in order to get these images. The user's eye movements can be either active or random eye movements.

Knowing the position of the eyeball center in CS-C, the gaze vector in CS-C can be calculated. An eye tracking session can start and keep calculating the gaze vector in CS-C.

During an eye tracking session, camera slippage caused by changes of its position relative to the user's eyeball center can be detected and corrected by keeping calculating and updating the position of the eyeball center in CS-C.

The orientation of the camera in the user head coordinate system CS-H is calculated in a camera-head calibration process. Step 1: the user picks a first gaze point at a distance and stares at it. Without changing the first gaze point, the user rotates the head about the X axis of the head, and the first set of gaze vectors associated with this rotation may be obtained. Then a vector vhcx that is aligned with the X axis of CS-H in CS-C can be obtained. Step 2: the user picks a second gaze point at a distance. Without changing the second gaze point, the user rotates the head about Y axis of the head, and a second set of gaze vectors associated with this rotation can be obtained. The first gaze point and the second gaze point may be the same or different. Then a vector vhcy aligned with the Y axis of CS-H in CS-C can be obtained. Step 3: the user looks straight ahead and picks a gaze point, and the gaze vector at this position is recorded. Then a vector vhcz aligned with the Z axis of CS-H in CS-C can be regarded as pointing to the negative direction of this gaze vector. Knowing any two axes of the X, Y, Z axes of a coordinate system, the third one can be calculated. Therefore, using vectors obtained from any of the three steps above, the orientation of the camera relative to the user's head can be calculated.

The gaze vector of the eye relative to the user's head can be calculated using a gaze vector in CS-C and an orientation of the camera relative to the user's head, i.e. orientation of CS-C relative to CS-H.

A number of configurations based on the above descriptions are also possible: Configuration A where one camera facing the user's eye is used; Configuration B where more than one camera facing a user's eye are used; Configuration C where one camera facing both of the user's eyes is used; Configuration D, which is a combination of Configuration A, Configuration B and Configuration C.

It is possible to: obtain the gaze vector of one eye using one camera with Configuration A; obtain the gaze vector of one eye using one camera with Configuration B; obtain the gaze vectors of both eyes using one camera for each eye with Configuration A; obtain the gaze vectors of both eyes using more than one camera for each eye with Configuration B; find the gaze vectors of both eyes using one camera with Configuration C; find the gaze vectors of both eyes with Configuration D.

Various hardware components may be used to implement the functions and processes in this disclosure. One hardware component is a camera. The camera may measure the brightness and color of light. The term "camera coordinate system" or "CS-C" is used interchangeably with the term "image sensor coordinate system" or "CS-I" in this disclosure. The camera can capture color images or grayscale images. The camera can capture infrared images or non-infrared (e.g., visible light) images. Parameters of a camera include its physical dimensions, resolution and focal length of its lens. A 2D camera image frame coordinate system is defined in Part A1.2 of the Appendix section.

One hardware component is a head gear that fixes the camera to the user's head. The head gear can be a glasses frame, a head band or a helmet, depending on the applications. Other forms of head gear is possible.

One hardware component is a computer such as an embedded system or a desktop system.

Figure 8:
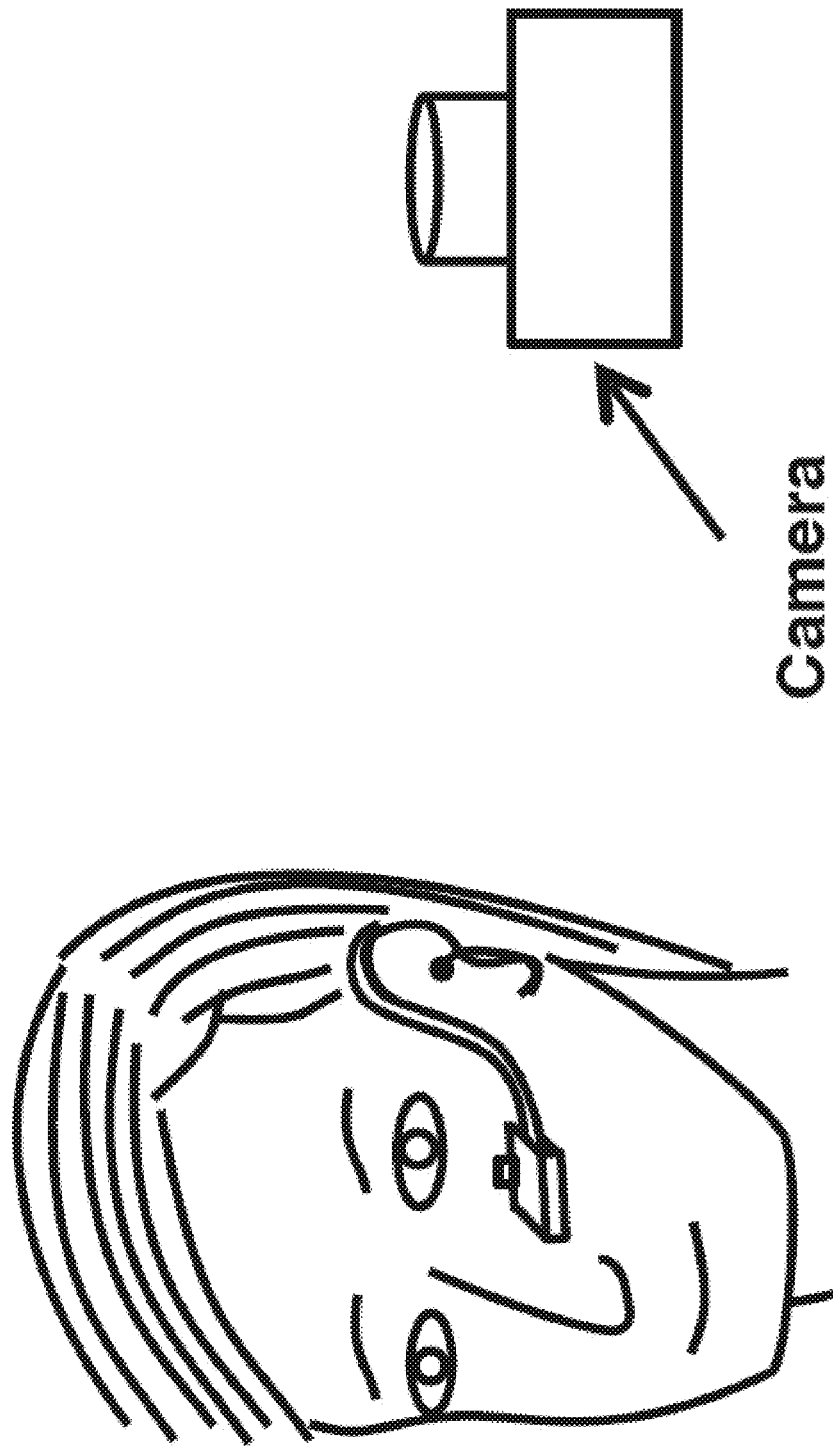
FIG. 8 shows that a camera is attached to a rigid frame so that its relative position and orientation do not change.

As shown in FIG. 8, a camera may be attached to a rigid frame so that its position and orientation relative to the user's head do not change. The gaze vectors of the user's eye may be calculated in the eye tracking mode.

Calculation of the position of eyeball center relative to the camera is described below.

The position of the eyeball center ("vec") in CS-C needs to be obtained before gaze vector can be calculated. To do so, a sequence of the images of the eye is captured by the camera. For each image, the contour of the pupil is extracted. The contour of a pupil can be considered as an ellipse. Having two or more ellipses representing the contours of the pupils from the image sequences, vec can be calculated. The detailed steps are described in Part C1, Part C2 of the Algorithms section.

Although two ellipses obtained from two eye images are sufficient for calculating vec, in practice, more accurate and robust results can be obtained if more ellipses from more eye images are used. To be more specific, using combinations among a set of eye images, more solutions for vec can be calculated. These solutions could be different due to measuring error and noise in the system. And these solutions can be further processed with certain methods to get result with better accuracy and robustness. Examples of these methods are averaging, least squares regression, Karmann Filter, etc.

Ideally the position and shape of the pupil should vary to enough extend from one eye image to another. To get the images of different positions of the pupil, the user can either stare at the fixed position, and turn the head to different directions, or hold the head in the fixed position, and roll the eyeball to look at different directions, or a combination the above two.

The ellipse obtained from the pupil contour in the eye image should be less like a circle. To be more specific, the ratio of the lengths of its semi-major axis a and semi-minor axis b (see the Appendix section) should be larger than a threshold, i.e., the following condition should be met: a/b>threshold.

Alternatively, instead of pupil, the limbus of the eye can be used for extracting the ellipse from the eye image. The ellipses extracted from limbus from two or more eye images can be used for calculating eyeball center vec in CS-C in the same way as the ellipses extracted from pupil from two or more images. It is also possible to use ellipses extracted from both pupil and limbus for flexibility and robustness.

Calculation of the Gaze Vector in Camera Coordinate System is described below. After the position of eyeball center vec is obtained, an eye tracking session can start. The gaze vector vgc in CS-C can be calculated from the captured eye image, to be more specific, from the position of the center of pupil pc detected from the eye image.

Assuming:
vec=(xc, yc, zc) be coordinate of the origin of CS-E in CS-C;
pc=(x, y) be the center of the pupil in camera image plane;
vgc=(xg, yg, zg) be the gaze vector in CS-C;
vgc can be calculated from vec and pc. Details can be found in Part C3 of the Algorithms section.

Slippage Detection and Correction is described here. The calculation of the position of eyeball center vec in CS-C can be done in either a separate stage or in parallel with eye tracking session. If the positions of eyeball center vec is calculated consecutively, possible camera slippage caused by changes of the camera's position relative to the eyeball center may be detected by comparing current value of vec against existing value. Camera slippage relative to eyeball center can be effectively detected during the eye tracking session. The vec may be updated as a parameter during the eye tracking session in real time.

Calibration of the Orientation of the Camera Relative to User Head is described below.

The orientation of the camera in the head coordinate system CS-H is calculated in a camera-head calibration process. The user is instructed to pick a gaze point at a distance and stare at it. Step 1, without changing the gaze point, the user rotates the head about X axis of the head, and the first set of gaze vectors associated with this rotation can be obtained. Then a vector vhcx that is aligned with X axis of CS-H in CS-C can be obtained. Step 2, the user either keeps the first gaze point or picks a new gaze point at a distance, and without changing the gaze point, rotates the head about Y axis of the head, and a second set of gaze vectors associated with this rotation can be obtained. Then a vector vhcy that is aligned with Y axis of CS-H in CS-C can be obtained. Step 3, the user can look straight ahead and pick a gaze point, the gaze vector at this position is recorded. Then a vector vhcz that is aligned with Z axis of CS-H in CS-C can be regarded as pointing to the negative direction of this gaze vector. Knowing any two axes of the X, Y, Z axes of a coordinate system, the third one can be calculated. Therefore, using vectors obtained from any of the above 3 steps, the orientation of camera relative to user head can be calculated.

In a calibration process in one embodiment is shown in FIG. 9 and FIG. 10. In FIG. 9, the user picks a distant gaze point. While staring at it, the user turns the head up and down. The camera captures the images of the eye, which show the positions of the pupil center related to different head positions. In FIG. 10, the user either keeps the first gaze point or picks a new gaze point at a distance, and without changing the gaze point, the user turns the head left and right. The camera captures the eye images which shows the position of the pupil related to different head positions.

In another calibration procedure, the user looks straight ahead and picks a distant gaze point. The gaze vector at this position is recorded. Then Z axis of CS-H in CS-C can be regarded as pointing to the negative direction of this gaze vector. Then the user can choose to perform first step in FIG. 9 and or second step in FIG. 10.

Assuming qch be the orientation quaternion of camera coordinate system in head coordination system, i.e. CS-C in CS-H. Details of calculating qch can be found in Part C4 of the Algorithms section.

More than two gaze vectors can be used for detecting either X or Y axis of CS-H in CS-C as described in Part C4.2 and Part C4.3 of the Algorithms section. Multiple pairs of gaze vectors can generate multiple solutions, which can be used to obtain a final result, using methods such as averaging, least squares regression or Karman filter etc. Similarly, more than one vector can be used for detecting the Z axis of CS-H in CS-C as described in Part C4.8 of the Algorithms section.

Calculation of Gaze Vector in Head Coordinate System is described below.

Knowing the gaze vector vgc that pointing from the origin of CS-E to the object user is looking at in the CS-C, and the orientation quaternion qch of CS-C in CS-H, the gaze vector vgh in CS-H can be calculated as vgh=qvq_trans(qch, vgc). See Part A2.3.6 of the Appendix section.

Figure 11A:
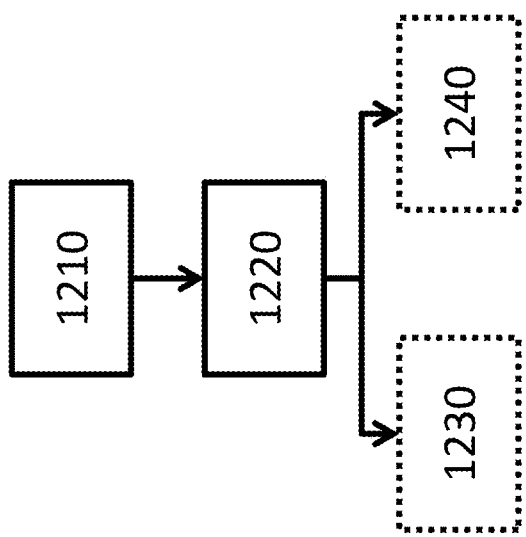
FIG. 11A schematically shows a flowchart of a method, according to an embodiment.

FIG. 11A schematically shows the flowchart of a method, according to an embodiment. In procedure 1210, a first image and a second image of a person's eye are obtained, with an imaging sensor. The image sensor may include one camera or more than one camera. The image sensor may obtain an image of one or both eyes of the person. The first image and the second image may be different. The first image and the second image may be obtained during an intentional or random movement of the eye. In procedure 1220, a position relationship between an eyeball center of the eye and the imaging sensor is determined based on the first image and the second image, for example, using a processor of a computing device. For example, contours of a pupil or a corneal limbus may be extracted from the first image and the second image (e.g., using the processor) and the position relationship may be determined based on the contours (e.g., using the processor). In optional procedure 1230, a relative movement of the imaging sensor with respect to the eyeball center is determined based on the position relationship, for example, using the processor. In optional procedure 1240, an orientation relationship between the imaging sensor and the person's head is determined, for example, using the processor.

Figure 11B:
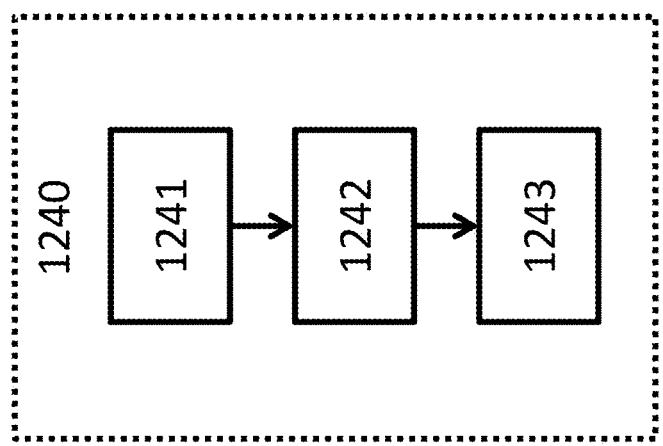
FIG. 11B shows a flowchart for an optional procedure in the flowchart of FIG. 11A.

FIG. 11B shows a flowchart for the optional procedure 1240. In procedure 1241, a first set of gaze vectors is obtained (e.g., using the processor) while the person's head rotates about a first axis and the eye maintains a first gaze point. In procedure 1242, a second set of gaze vectors is obtained (e.g., using the processor) while the person's head rotates about a second axis and the eye maintains a second gaze point; or a third gaze vector is obtained (e.g., using the processor) while the eye maintains a third gaze point. In procedure 1243, the orientation relationship is determined (e.g., using the processor) based on the first set of gaze vectors, and based on the second set of gaze vectors or the third gaze vector.

Figure 12:
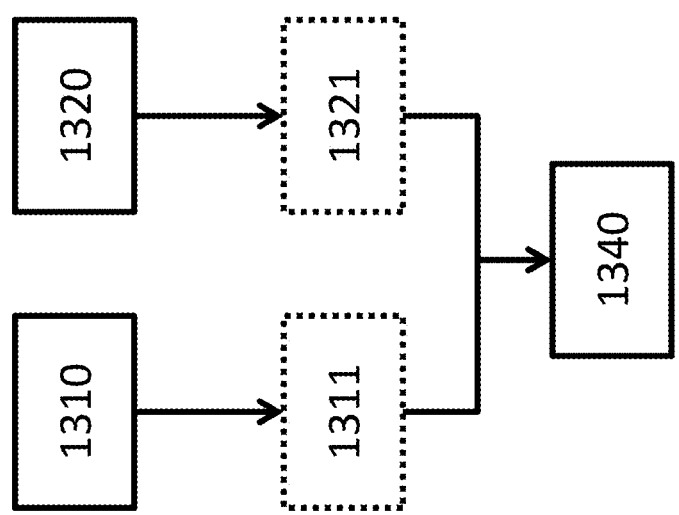
FIG. 12 schematically shows a flowchart of a method, according to another embodiment.

FIG. 12 schematically shows the flowchart of a method, according to another embodiment. In procedure 1310, a first set of images of a person's eye is obtained using an imaging sensor, while the person's head rotates about a first axis and the eye maintains a first gaze point. The image sensor may include one camera or more than one camera. The image sensor may obtain an image of one or both eyes of the person. In optional procedure 1311, a first set of gaze vectors is obtained (e.g., using a processor of a computing device) based on the first set of images. In procedure 1320, a second set of images of the eye is obtained using the imaging sensor, while the person's head rotates about a second axis and the eye maintains a second gaze point; or a third image is obtained using the imaging sensor, while the eye maintains a third gaze point. In optional procedure 1321, a second set of gaze vectors is obtained (e.g., using the processor) based on the second set of images; or a third gaze vector is obtained (e.g., using the processor) based on a third image. In procedure 1340, an orientation relationship between the imaging sensor and the person's head is determined (e.g., using a processor of a computing device), based on the first set of images, and based on the second set of images or the third image (e.g., based on the first set of gaze vectors, the second set of gaze vectors and the third gaze vector, which are respectively obtained from the first set of images, the second set of images and the third image). The first gaze point and the second gaze point may be different or the first gaze point and the third gaze point may be different.

Algorithms

C1. Calculating location of the eyeball center image in camera 2D image plane

Given an image of the eye, assuming the contour of the pupil can be extracted. The shape of the pupil contour can be regarded as an ellipse. (see Part A4 of the Appendix section.)

Figure 4:
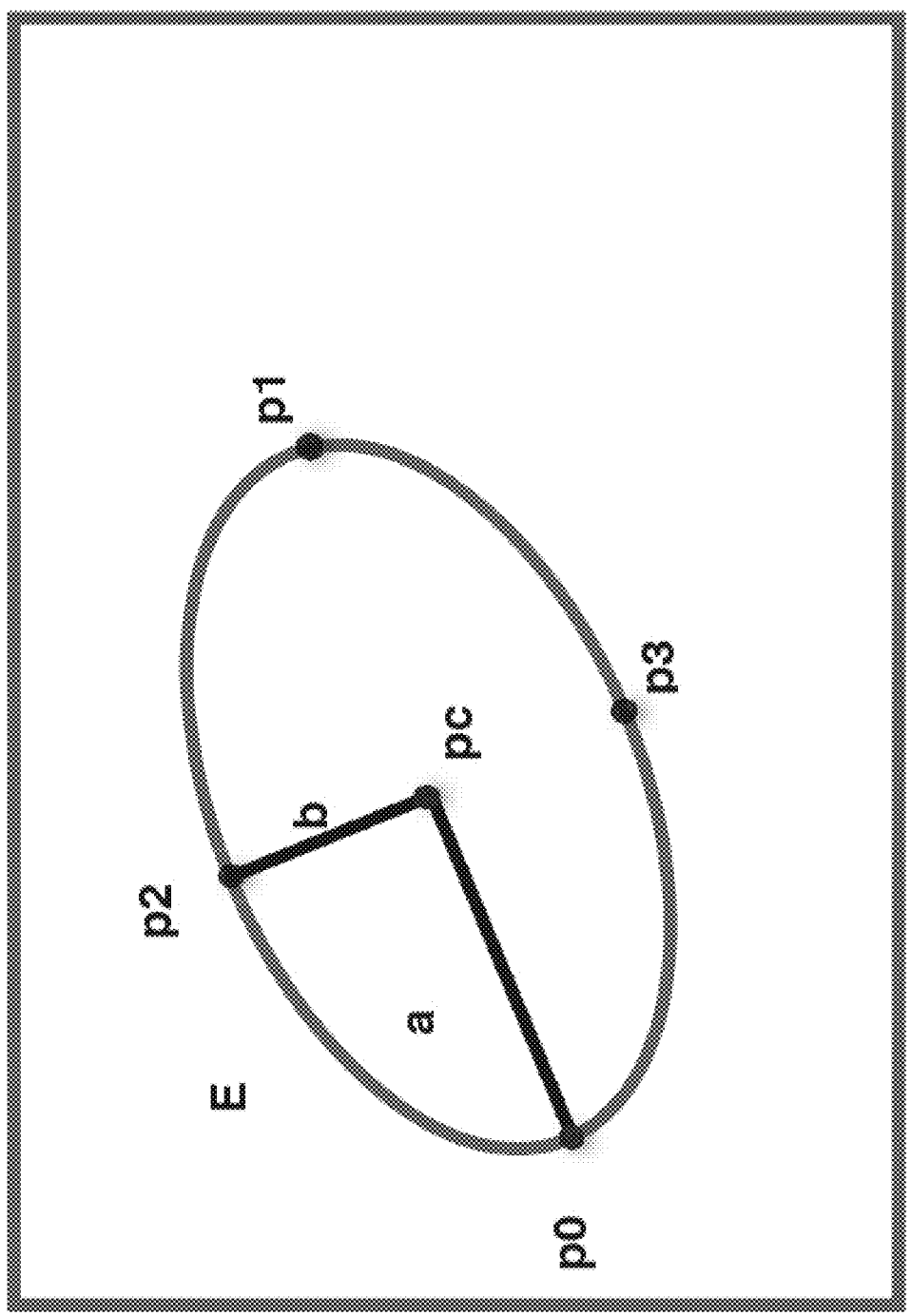
FIG. 4 shows an ellipse in a 2D space.

An ellipse in 2D space can be represented by its vertices and co-vertices, as shown in FIG. 4.

Figure 5:
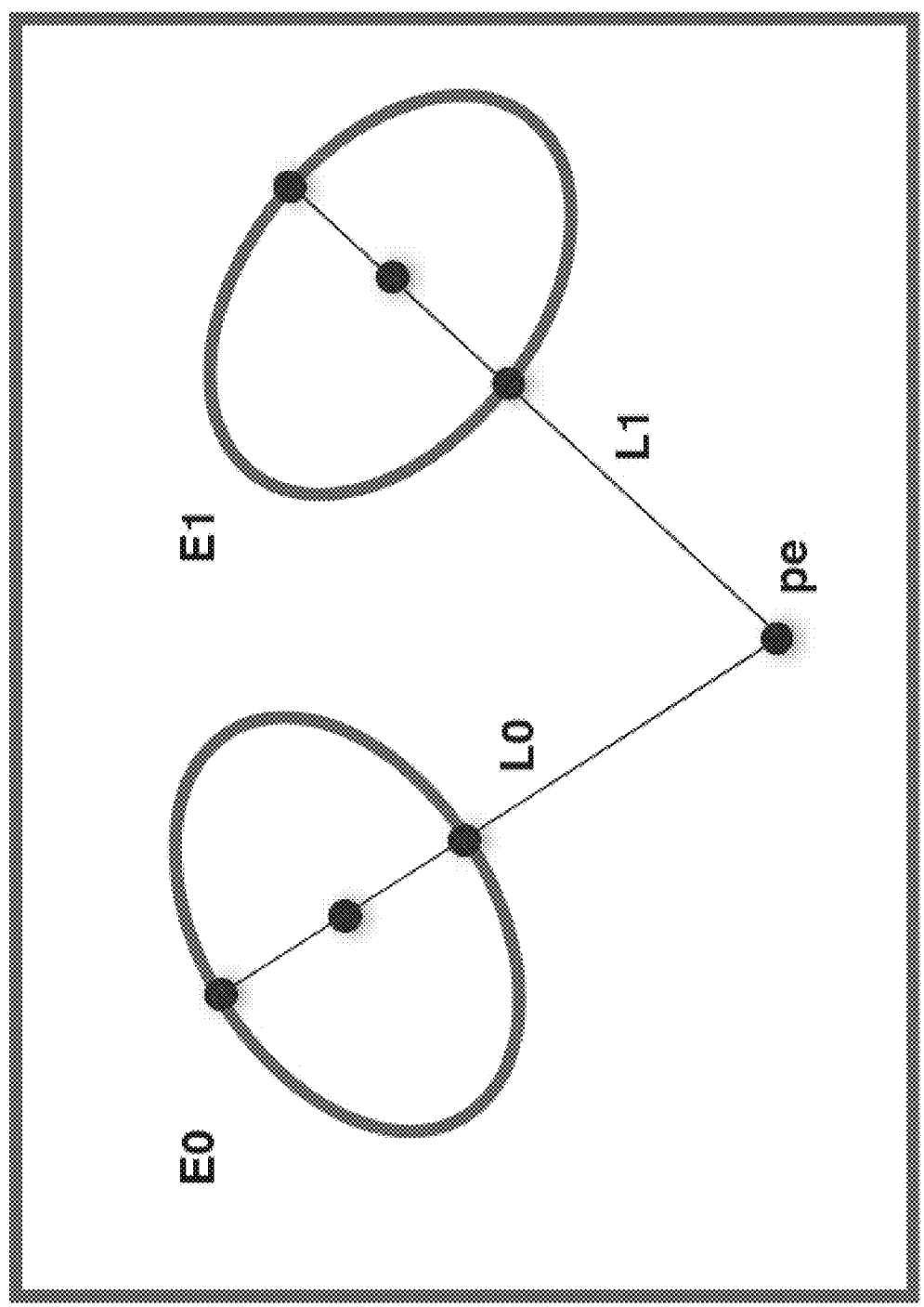
FIG. 5 shows that having at least two images of the pupil at different positions, the point of eyeball center image in camera 2D image plane can be calculated.

Although the eyeball center is not visible from the camera, having at least 2 images of the pupil at different positions, as shown in FIG. 5, the point pe of eyeball center image in camera 2D image plane can be calculated. Assuming:

E0 being ellipses extracted from the pupil in the eye images at time t0;

E1 being ellipses extracted from the pupil in the eye images at time t1.

Assuming:

L0 being the line passing the 2 co-vertices of E0;

L1 being the line passing the 2 co-vertices of E1.

The method to obtain the linear equation of L0 and L1 is in Part A3.1 of the Appendix section.

pe can be calculated as the intersection point of L0 and L1 (see Part A3.2 of the Appendix section).

C2. Calculating the position of the eyeball center in CS-C

Assuming we have an ellipse E representing the contour of the pupil in a captured eye image, assuming E is defined by its vertices and co-vertices as described in FIG. 4;

p0, p1 being the 2 points at the ends of its 2 vertices, the order is not important;

p2, p3 being the 2 points at the ends of its 2 co-vertices, the order is not important;

pc being the center point of the ellipse, it can be calculated from p0, p1, p2, p3 (see Part A 4.2 of the Appendix section); and pe being the eyeball center image point obtained from Part C1 of the Algorithms section.

The above 6 points in the 2D camera image plane can be each converted into its related 3D unit vector pointing from the origin of CS-C to its image point in camera 2D image plane, as described in Part A.1.3 of the Appendix section.

$v0 = v\_frm\_p(p0)$ $v1 = v\_frm\_p(p1)$ $v2 = v\_frm\_p(p2)$ $v3 = v\_frm\_p(p3)$ $vc = v\_frm\_p(pc)$ $ye = vjrm\_p(pe)$ $\cos\_long = v\_dot(v0, v1)$ $\cos\_short = v\_dot(v2, v3)$ $\tan\_long\_h = \sqrt{(1-\cos\_long)/(1+\cos\_long)}$ $\tan\_short\_h = \sqrt{(1-\cos\_short)/(1+\cos\_short)}$ $\cos\_alfa = v\_dot(vc, ye)$ $\sin\_beta = \tan\_short\_h/\tan\_long\_h$ $\sin\_r = \sqrt{1-\cos\_alfa*\cos\_alfa}$ $\sin\_d = \sqrt{1-\sin\_beta*\sin\_beta}$ $dist = \sin\_d/\sin\_r$ Knowing:

ve, the unit vector that points from origin of CS-C to the eyeball center in CS-C, dist, the distance from the origin of CS-C to eyeball center in CS-C, vec, the position of the eyeball center in CS-C can be obtained as:

$vec = (x, y, z)$ where:

$x = xe*dist$ $y = ye*dist$ $z = ze*dist$ $ve = (xe, ye, ze)$

C3. Calculating Gaze Vector in Camera Coordinate System

Assuming the position of eyeball center has be obtained with the method described in Part C1 of the Algorithms section and Part C2 of the Algorithms section, where:

vec=(xc, yc, zc) be the coordinates of the origin of CS-E in CS-C pc=(x, y) be the center of eye pupil in camera image frame coordinate system (see Part A1.2 of the Appendix section)

vgc=(xg, yg, zg) be the gaze vector that pointing from the origin of CS-E to the gaze point in CS-C. vgc can be calculated as:

$h=-DEFOX(x)$(see Part A1.3 of the Appendix section)

$v=-DEFOY(y)$ $a=h*h+v*v+1$ $b=2*((a-1)*zc-h*xc-v*yc)$ $c=(xc-h*zc)*(xc-h*zc)+(yc-v*zc)*(yc-v*zc)-1$ $p=b*b-4*a*c$ $k=sqrt(p)$ $z1=(-b+k)/(2*a)$ $z2=(-b-k)/(2*a)$ Both z1 and z2 are candidates of the solution of zv, z1 is picked as z2 is pointing away from the camera. Therefore, we have:

$zg=z1$ $xg=h*(zc+zg)-xc$ $yg=v*(zc+zg)-yc$

C4. Obtaining the Orientation of the Camera Relative to User Head

Assuming the position of eyeball center are known, and gaze vector vgc in CS-C can be calculated. The goal is to get the orientation quaternion qch of CS-C in CS-H.

C4.1 In one calibration procedure, the user picks a distant gaze point. By staring at it, the user first rotate about the X axis of CS-H, getting the first and second gaze vector v0 and v1 related this axis. And then the user either keeps the first gaze point or picks a new gaze point at a distance and stares at it, without changing the gaze point, the user rotates about the Y axis of CS-H, getting the first and second gaze vector v2 and v3 on this axis. v0, v1, v2 and v3 are in CS-C.

C4.2 The vector vhcx that is aligned with X axis of CS-H in CS-C can be calculated:

$v10=v\_crs(v1,v0)$ $vhcx=v\_uni(v10)$

C4.3 The vector vhcy that is aligned with Y axis of CS-H in CS-C can be calculated:

$v32=v\_crs(v3,v2)$ $vhcy=v\_uni(v32)$

C4.4 Knowing vhcx and vhcx, the 3×3 matrix mhc from CS-H to CS-C can be calculated:

$vx=vhcx$ $vz=v\_crs(vhcx,vhcy)$ $vy=v\_crs(vz,vx)$ $mhc=mjrm\_v(vx,vy,vz)$

C4.5 Knowing mhc, the quaternion qch from CS-C to CS-H can be calculated:

$qhc=q\_frm\_m(mhc)$ $qch=q\_cnj(qhc)$

C4.6 It is noted the user can also first rotate about the Y axis of CS-H, getting the first and second gaze vector v2 and v3 about this axis. And then the user rotates about the X axis of CS-H, getting the first and second gaze vector v0 and v1 on this axis. v0, v1, v2 and v3 in CS-C. The rest of the steps are the same.

C4.7 It is noted that more than 2 vectors can be used to calculate either vhcx or vhcy as described in C4.2 and C4.3. Taking vhcx as an example, if multiple pairs of gaze vectors are used, assuming we have multiple solutions as vhcx0, vhcx1, vhcx2 and so on. Using some well-known methods such as averaging, least squares regression or Karman filter etc., a final result vhcx can be calculate based on these solutions. Same is true for vhcy.

C4.8 In another calibration procedure, the user looks straight ahead and picks a distant gaze point. The gaze vector at this position is recorded. Then Z axis of CS-H in CS-C can be regarded as pointing to the negative direction of this gaze vector. We can obtained vector vhcz that is aligned with Z axis of CS-H in CH-C. The orientation of CS-H in CH-C can be calculated from any 2 vectors from vhcx, vhcy and vhcz as the third can be calculated from these 2 vectors. vhcx and/or vhcy can be obtained (see Part C4.1 of the Algorithms section). The procedure to calculate qch is similar to what's described in Part C4.2 to Part C4.5 of the Algorithms section).

APPENDIX

The mathematics tools listed in Appendix are used in the algorithms.

A1. Coordinate Systems

Figure 2:
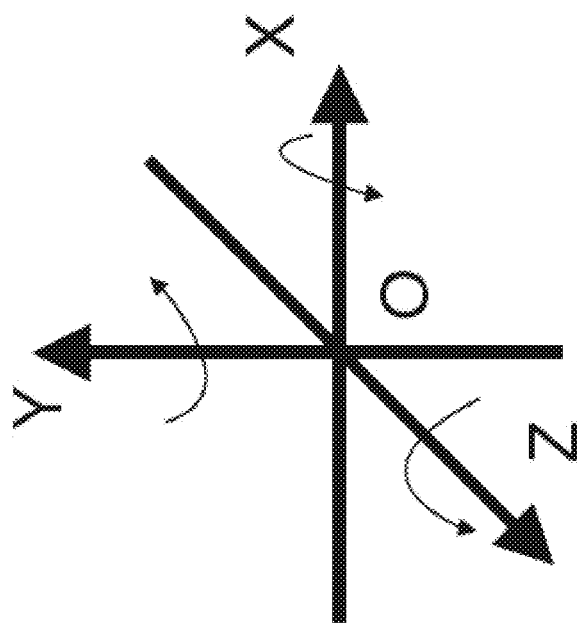
FIG. 2 shows a 3D coordinate system.

A1.1 A 3D coordinate system has 3 axes, X, Y and Z, as shown in FIG. 2. Right hand rule is applied for the order of the axes and the positive rotation directions.

Any 2 axes can form a plane. Therefore, there are 3 planes defined as P-XY, P-YX and P-ZX planes.

Figure 1:
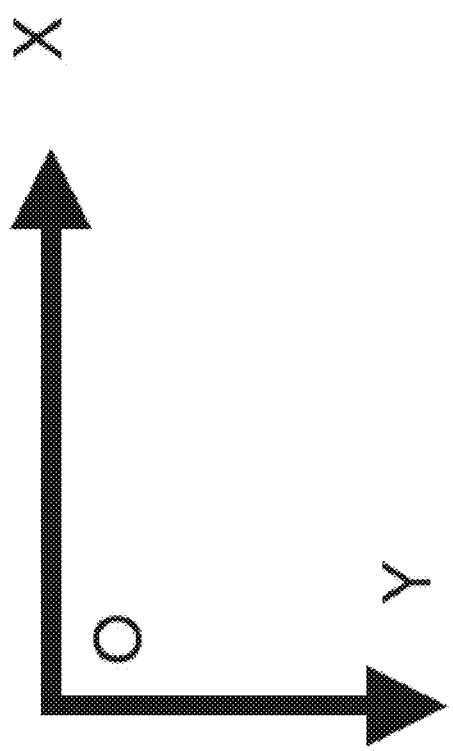
FIG. 1 shows a two-dimensional (2D) coordinate system.

A1.2 A 2D coordinate system for camera image frame has 2 axes, X, Y, as shown in FIG. 1.

A1.3. Converting a point in 2D camera image frame coordinate system to 3D camera coordinate system.

A 3D camera coordinate system has x axis pointing to the right, y axis pointing to the top and z axis pointing to the opposite direction of the lens.

The 2D image plane can be considered:
Being parallel to the XY plan of the CS-C
With its origin at its top-left corner
With its image center sitting at (0, 0, −1) of CS-C
With its X axis being parallel to the X axis of CS-C, pointing to the same direction
With its Y axis being parallel to the Y axis of CS-C, pointing to the opposite direction
With different unit from CS-C. To be more specific, FOCAL_LEN is the focal length of the camera in unit of pixel counts.

A unit vector vu pointing from the origin of the CS-C to the point p in the camera image 2D plane can be calculated:

$vu=v\_frm\_p(p)$ where:

$p=(x,y)$ $vu=(vx,vy,vz)$ where $vu=v\_uni(v)$ $v=(h,v,-1.0)$ where $h=DEFOX(x)=(x-x\_center)/FOCAL\_LEN$ $v=DEFOY(y)=(y\_center-y)/FOCAL\_LEN$ where
(x_center, y_center) is the coordinates of the center of the camera image 2D frame.

A1.4. A point in 3D Coordinates can be represented by a 3D vector v=(x, y, z). The vector is from the origin of the coordinate system to the position of the point.

A2. Quaternion, 3D Vector, 3×3 Matrix and 2D Vector Mathematics

A2.1.1 A Quaternion has 4 Elements $q=(w,x,y,z)$

A2.1.2 an Identity Quaternion:

$q=q\_idt(q)=(1,0,0,0)$

A2.1.3 The conjugation of a quaternion:

$q\_cnj(q)=(w,-x,-y,-z)$

A2.1.4 The length of a quaternion:

$q\_len(q)=\text{sqrt}(w*w+x*x+y*y+z*z)$ sqrt( ) is square root of a floating point number A2.1.5 A Unit Quaternion has a Length of 1
To unitize a quaternion q:

$u=q\_uni(q)$ where $q=(w,x,y,z)$ $u=(uw,ux,uy,uz)$ $uw=x/len$ $ux=x/len$ $uy=y/len$ $uz=z/len$ $len=q\_len(q)$ A2.1.6 the Product of 2 Quaternions q and p $t=q\_prd2(q,p)=q*p$ where $q=(qw,qx,qy,qz)$ $p=(pw,px,py,pz)$ $t=(tw,tx,ty,tz)$ and $tw=(qw*pw-qx*px-qy*py-qz*pz)$ $tx=(qw*px+qx*pw+qy*pz-qz*py)$ $ty=(qw*py-qx*pz+qy*pw+qz*px)$ $tz=(qw*pz+qx*py-qy*px+qz*pw)$ As a quaternion can be used to represent a rotation transformation, if q2 is product of 2 quaternion q2=q_prd2 (q1, q0), then applying q2 as a orientation transformation is equivalent to applying q0 and then q1.

A2.1.7 The Product of 3 Quaternions $q=q\_prd3(q1,q2,q3)=q\_prd2(q1,q\_prd2(q2,q3))$ A2.1.8 The Product of 4 Quaternions $q=q\_prd4(q1,q2,q3,q4)=q\_prd2(q1,q\_prd3(q2,q3,q4))$ A2.2.1 A 3D Vector has 3 Elements $v=(x,y,z)$ A2.2.2 The length of a 3D vector:

$v\_len(v)=\text{sqrt}(x*x+y*y+z*z)$

A2.2.3 A unit 3D vector has a length of 1
To untize a 3D vectors v:

$u=v\_uni(v)$ where $v=(x,y,z)$ $u=(ux,uy,uz)$ $ux=x/len$ $uy=y/len$ $uz=z/len$ $len=v\_len(v)$ A2.2.4 A unit quaternion can be interpreted as a combination of rotation vector and an angle rotating about this vector:

$q=(w,x,y,z)$ v=(vx,vy,vz) is the rotation vector
theta is the rotation angle
where $w=\cos(\text{theta}/2)$ $x=vx*\sin(\text{theta}/2)$ $y=vy*\sin(\text{theta}/2)$ $z=vz*\sin(\text{theta}/2)$ A2.2.5 Dot product of 2 3D vectors va, vb:

$d=v\_dot(va,vb)=va \cdot vb=ax*bx+ay*by+az*bz$ where $va=(ax,ay,az)$ $vb=(bx,by,bz)$ There is an important property of vector dot product, Assuming theta to be angle between va and vb:
Then: cos(theta)=v_dot(va,vb)

A2.2.6 Cross product of 2 3D vectors va, vb:

$vc = v\_crs(va, vb) = va \times vb$ where $va = (ax, ay, az)$ $vb = (bx, by, bz)$ $vc = (cx, cy, cz)$ $cx = ay*bz - az*by$ $cy = az*bx - ax*bz$ $cz = ax*by - ay*bx$

A2.3.1 3×3 Matrix $$m = \begin{pmatrix} Xx & Yx & Zx \\ Xy & Yy & Zy \\ Xz & Yz & Zz \end{pmatrix}$$

A2.3.2 Identity 3×3 Matrix $$m = \text{m\_idt}() == \begin{pmatrix} 1 & 0 & 0 \\ 0 & 1 & 0 \\ 0 & 0 & 1 \end{pmatrix}$$

A2.3.3 Matrix Subtraction $$m2 = \text{m\_sub}(m1, m0) = m1 - m0 = \begin{pmatrix} Xx1 - Xx0 & Yx1 - Yx0 & Zx1 - Zx0 \\ Xy1 - Xy0 & Yy1 - Yy0 & Zy1 - Zy0 \\ Xz1 - Xz0 & Yz1 - Yz0 & Zz1 - Zz0 \end{pmatrix}$$

$$m1 = \begin{pmatrix} Xx1 & Yx1 & Zx1 \\ Xy1 & Yy1 & Zy1 \\ Xz1 & Yz1 & Zz1 \end{pmatrix}$$

$$m0 = \begin{pmatrix} Xx0 & Yx0 & Zx0 \\ Xy0 & Yy0 & Zy0 \\ Xz0 & Yz0 & Zz0 \end{pmatrix}$$

A2.3.4 Matrix Vector Multiplication $vd = \text{mv\_prd}(m, v) = m * vs$ $$m = \begin{pmatrix} Xx & Yx & Zx \\ Xy & Yy & Zy \\ Xz & Yz & Zz \end{pmatrix}$$

$vs = (x, y, z)$ $vd = (dx, dy, dz)$ where:

$dx = Xx*x + Yx*y + Zx*z$ $dy = Xy*x + Yy*y + Zy*z$ $dz = Xz*x + Yz*y + Zz*z$

A2.3.5 Matrix from Quaternion $m = \text{m\_frm\_q}(q)$ $q = (qw, qx, qy, qz)$ where m is a 3×3 matrix $$m = \begin{pmatrix} Xx & Yx & Zx \\ Xy & Yy & Zy \\ Xz & Yz & Zz \end{pmatrix}$$

and $Xx = 1.0f - 2.0f*qy*qy - 2.0f*qz*qz$ $Xy = 2.0f*qx*qy + 2.0f*qw*qz$ $Xz = 2.0f*qx*qz - 2.0f*qw*qy$ $Yx = 2.0f*qx*qy - 2.0f*qw*qz$ $Yy = 1.0f - 2.0f*qx*qx - 2.0f*qz*qz$ $Yz = 2.0f*qy*qz + 2.0f*qw*qx$ $Zx = 2.0f*qx*qz + 2.0f*qw*qy$ $Zy = 2.0f*qy*qz - 2.0f*qw*qx$ $Zz = 1.0f - 2.0f*qx*qx - 2.0f*qy*qy$

A2.3.6 Transform a 3D Vectors v with a Quaternion q:

$vd = qvq\_\text{trans}(q, vs) = \text{mv\_prd}(m, vs)$ where
q is a quaternion
vs is the source 3D vector
vd is the result 3D vector
m is a 3×3 matrix $m = \text{m\_frm\_q}(q)$

A2.3.7 Matrix by Rotating x Axis $m = \text{m\_frm\_x\_axis\_sc}(s, c)$ where $$m = \begin{pmatrix} Xx & Yx & Zx \\ Xy & Yy & Zy \\ Xz & Yz & Zz \end{pmatrix}$$

$s = \sin(\text{theta})$ $c = \cos(\text{theta})$ and $Xx = 1.0$ $Yx = 0.0$ $Zx = 0.0$ $Xy = 0.0$ $Yy = c$ $Zy = -s$ $Xz = 0.0$ $Yz = s$ $Zz = c$

A2.3.8 Matrix by Rotating y Axis $m = m\_frm\_y\_axis\_sc(s,c)$ where $$m = \begin{pmatrix} Xx & Yx & Zx \\ Xy & Yy & Zy \\ Xz & Yz & Zz \end{pmatrix}$$

$s = \sin(\text{theta})$ $c = \cos(\text{theta})$ and $Xx = c$ $Yx = 0.0$ $Zx = s$ $Xy = 0.0$ $Yy = 1.0$ $Zy = 0.0$ $Xz = -s$ $Yz = 0.0$ $Zz = c$

A2.3.9 Quaternion from Matrix $q = q\_frm\_m(m)$ where $q = (w, x, y, z)$ $$m = \begin{pmatrix} Xx & Yx & Zx \\ Xy & Yy & Zy \\ Xz & Yz & Zz \end{pmatrix}$$

and:

```
if(Zz < 0) {
    if (Xx > Yy) {
        t = 1 + Xx - Yy - Zz
        w = Yz - Zy
        x = t
        y = Xy + Yx
        z = Zx + Xz
    } else {
        t = 1 - Xx + Yy - Zz
        w = Zx - Xz
        x = Xy + Yx
        y = t
        z = Yz + Zy
    }
} else {
    if(Xx < -Yy) {
        t = 1 - Xx - Yy + Zz
        w = Xy - Yx
        x = Zx + Xz
        y = Yz + Zy
        z = t
    } else {
        t = 1 + Xx + Yy + Zz
        w = t
        x = Yz - Zy
        y = Zx - Xz
        z = Xy - Yx
    }
}
```

A2.3.9 Matrix from Vector $m = m\_frm\_v(vx, vy, vz)$ where $$m = \begin{pmatrix} Xx & Yx & Zx \\ Xy & Yy & Zy \\ Xz & Yz & Zz \end{pmatrix}$$

$vx = (Xx, Xy, Xz)$ $vy = (Yx, Yy, Yz)$ $vz = (Zx, Zy, Zz)$

A2.4.1 A Point in 2D Space is Also a 2D Vector, it has 2 Elements $p = (x, y)$

A2.2.2 The distance d between 2 2D points pa, pb is:

$d = p\_dist(pa, pb) = \text{sqrt}((xa-xb)*(xa-xb) + (ya-yb)*(ya-yb))$ where $pa = (xa, ya)$ $pb = (xb, yb)$ A2.2.3 The length of a 2D vector:

$p\_len(p) = \text{sqrt}(x*x + y*y)$

A2.2.4 A Unit 2D Vector has a Length of 1
To unitize a 2D vectors p:

$u = p\_uni(p)$ where $p = (x, y)$ $u = (ux, uy)$ $ux = x/len$ $uy = y/len$ $len = p\_len(v)$ A2.2.5 Dot product of 2 2D vectors pa, pb:

$d = p\_dot(pa, pb) = xa*xb + ya*yb$ where $pa = (xa, ya)$ $pb = (xb, yb)$

There is an important property of vector dot product,
Assuming theta to be angle between pa and pb:
Then: cos(theta)=p_dot(pa,pb)

A3. Line in 2D Space

A3.1 Two-Point Form of a Line in 2D Space

Figure 3:
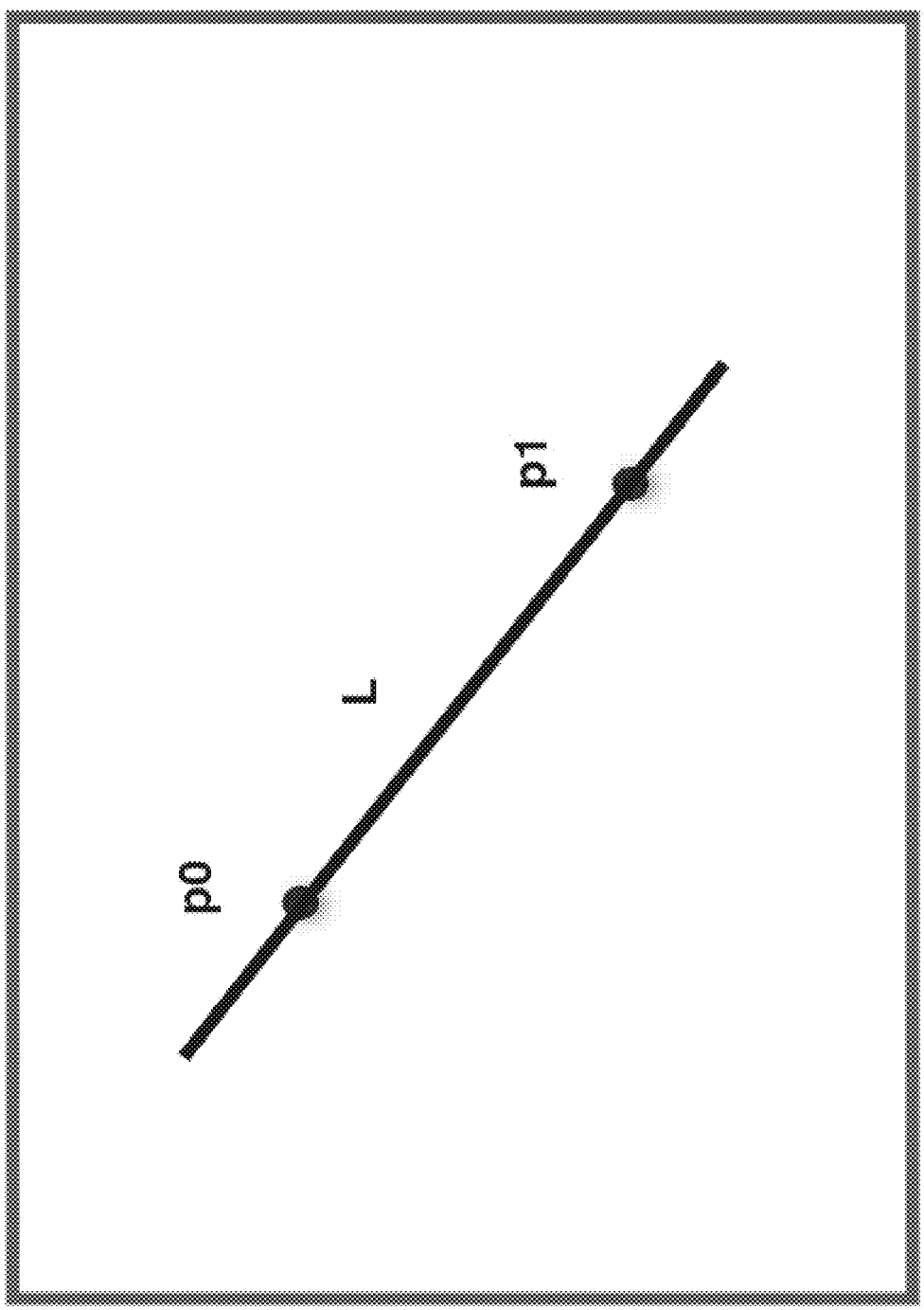
FIG. 3 shows a line in a 2D space.

As shown in FIG. 3, a line L in 2D space can be represented by 2 of points p0 and p1 that it passes:

Linear equation of L:

$$L: y = m*x + b$$

where:

$$m = (y1 - y0)/(x1 - x0)$$

$$b = y0 - x0*(y1 - y0)/(x1 - x0)$$

$$p0 = (x0, y0)$$

$$p1 = (x1, y1)$$

A3.2 Intersection p of 2 Lines L0, L1

Knowing the linear equations of L0 and L1:

$$L0: y = m0*x + b0$$

$$L1: y = m1*x + b1$$

Their intersection can be calculated as:

$$p = (x, y)$$

where $$x = (b1 - m1)/(m0 - b0)$$

$$y = (m0*b1 - b0*m1)/(m0 - b0b)$$

note:

L0 and L1 are parallel if a==b

A4. Ellipse in 2D Space

A4.1 As shown in FIG. 4 an ellipse E can be represented by any 3 of the following two pairs of points:

vertex: p0, p1 co-vertex: p2, p3

A4.2 The center of the ellipse pc can be calculated as:

$$pc = (x, y)$$

$$x = (x0 + x1)/2 \text{ or } (x2 + x3)/2$$

$$y = (y0 + y1)/2 \text{ or } (y2 + y3)/2$$

where:

$$p0 = (x0, y0)$$

$$p1 = (x1, y1)$$

$$p2 = (x2, y2)$$

$$p3 = (x3, y3)$$

A4.3 Semi-Major Axis a, and Semi-Minor Axis b $$a = q\_dist(p0, p1)$$

$$b = q\_dist(p2, p3)$$

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize that the present teachings are amenable to a variety of modifications and/or enhancements.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method comprising:
    obtaining a first image and a second image of a person's eye, with an imaging sensor;
    determining a position relationship between an eyeball center of the eye and the imaging sensor based on the first image and the second image;
    wherein determining the position relationship comprises extracting contours of a pupil or a corneal limbus from the first image and the second image, and determining the position relationship based on the contours;
    wherein determining the position relationship based on the contours comprises determining a location of the eyeball center in a 2D image plane of the imaging sensor based on the contours.

2. The method of claim 1, further comprising determining a relative movement of the imaging sensor with respect to the eyeball center based on the position relationship.

3. The method of claim 1, wherein the first image and the second image are different.

4. The method of claim 1, wherein the first image and the second image are obtained during an intentional or random movement of the eye.

5. The method of claim 1, further comprising determining an orientation relationship between the imaging sensor and the person's head.

6. The method of claim 1, wherein the imaging sensor comprises more than one camera.

7. The method of claim 1, wherein the imaging sensor is configured to obtain an image of more than one eye of the person.

8. An apparatus comprising:
    an imaging sensor configured to obtain a first image and a second image of a person's eye; and
    a computing device comprising a processor configured to determine a position relationship between an eyeball center of the eye and the imaging sensor based on the first image and the second image;
    wherein the processor is further configured to determine the position relationship by extracting contours of a pupil or a corneal limbus from the first image and the second image, and by determining the position relationship based on the contours;
    wherein the processor is further configured to determine the position relationship based on the contours by determining a location of the eyeball center in a 2D image plane of the imaging sensor based on the contours.

9. The apparatus of claim 8, wherein the processor is further configured to determine a relative movement of the imaging sensor with respect to the eyeball center based on the position relationship.

10. The apparatus of claim 8, wherein the first image and the second image are different.

11. The apparatus of claim 8, wherein the imaging sensor is configured to obtain the first image and the second image during an intentional or random movement of the eye.

12. The apparatus of claim 8, wherein the processor is further configured to determine an orientation relationship between the imaging sensor and the person's head.

13. The apparatus of claim 8, wherein the imaging sensor comprises more than one camera.

14. The apparatus of claim 8, wherein the imaging sensor is configured to obtain an image of more than one eye of the person.

15. A method comprising:
- obtaining a first image and a second image of a person's eye, with an imaging sensor;
- extracting a first contour of a pupil or a corneal limbus from the first image and extracting a second contour of the pupil or the corneal limbus from the second image;
- determining a location of an eyeball center of the eye in a 2D image plane of the imaging sensor based on the first contour and the second contour;
- determining a position relationship between the eyeball center and the imaging sensor based on the first contour, the second contour and the location.

16. An apparatus comprising:
- an imaging sensor configured to obtain a first image and a second image of a person's eye;
- a computing device comprising a processor configured to extract a first contour of a pupil or a corneal limbus from the first image and a second contour of the pupil or the corneal limbus from the second image, to determine a location of an eyeball center of the eye in a 2D image plane of the imaging sensor based on the first contour and the second contour, and to determine a position relationship between the eyeball center and the imaging sensor based on the first contour, the second contour and the location.

\* \* \* \* \*